United States Patent
Harpak et al.

(10) Patent No.: US 9,895,533 B2
(45) Date of Patent: Feb. 20, 2018

(54) IMPEDANCE MONITORING DURING ELECTROSTIMULATION

(71) Applicant: THERANICA BIO-ELECTRONICS LTD., Netanya (IL)

(72) Inventors: Amnon Harpak, Holon (IL); Uzi Hizi, Herzliya (IL)

(73) Assignee: THERANICA BIO-ELECTRONICS LTD., Netanya (IL)

( * ) Notice: Subject to any disclaimer, the term of this patent is extended or adjusted under 35 U.S.C. 154(b) by 0 days.

(21) Appl. No.: 14/992,046

(22) Filed: Jan. 11, 2016

(65) Prior Publication Data
US 2017/0197077 A1   Jul. 13, 2017

(51) Int. Cl.
| | |
|---|---|
| A61N 1/00 | (2006.01) |
| A61N 1/08 | (2006.01) |
| A61N 1/36 | (2006.01) |
| A61B 5/00 | (2006.01) |
| A61N 1/04 | (2006.01) |

(52) U.S. Cl.
CPC .............. *A61N 1/08* (2013.01); *A61B 5/6843* (2013.01); *A61N 1/0452* (2013.01); *A61N 1/0456* (2013.01); *A61N 1/36014* (2013.01); *A61N 2001/083* (2013.01)

(58) Field of Classification Search
CPC ......................... A61N 1/08; A61N 1/18; A61N 1/36–1/36028; A61N 1/36128; A61N 1/36139; A61N 1/37; A61N 1/3702; A61N 2001/083; A61N 2001/18
See application file for complete search history.

(56) References Cited

U.S. PATENT DOCUMENTS 4,613,850 A * 9/1986 Timmermann .......... A61N 1/08
128/908
6,217,574 B1   4/2001 Webster
(Continued)

OTHER PUBLICATIONS

Degen et al., "An improved Method to continuously monitor the Electrode-Skin Impedance during Bioelectric Measurements", Proceedings of the 29th Annual International Conference of the IEEE EMBS Cité Internationale, Lyon, France , pp. 6294-6297, Aug. 23-26, 2007.
(Continued)

*Primary Examiner* — Scott Getzow
(74) *Attorney, Agent, or Firm* — Sughrue Mion, PLLC (57) ABSTRACT

Embodiments described herein include a controller (22). The controller includes at least one interface (62) that couples the controller to stimulation circuitry (24), which includes a pair of electrodes (26a, 26b), and to measuring circuitry, and further includes controller circuitry (64). While the electrodes are coupled to skin (60) of a subject, the controller circuitry, via the interface, drives the stimulation circuitry to (i) pass a plurality of stimulating pulses (32) between the electrodes, and (ii) pass one or more reference pulses (34) between the electrodes, the reference pulses being different from each of the stimulating pulses. The controller receives, from the measuring circuitry, an impedance between the electrodes that is measured using the reference pulses. In response to the impedance measured using the reference pulses, but not in response to any impedance measured using the stimulating pulses, the controller circuitry controls the stimulation procedure. Other embodiments are also described.

26 Claims, 3 Drawing Sheets

(56) References Cited

U.S. PATENT DOCUMENTS

| | | |
|---|---|---|
| 8,620,434 B2 | 12/2013 | Bodlaender et al. |
| 2004/0015212 A1 | 1/2004 | Huber et al. |
| 2011/0264171 A1 | 10/2011 | Torgerson |
| 2013/0093501 A1* | 4/2013 | Kajimoto ........... A61N 1/36014 327/517 |
| 2014/0031895 A1 | 1/2014 | Rahimi et al. |
| 2014/0296934 A1 | 10/2014 | Gozani et al. |
| 2015/0257970 A1 | 9/2015 | Mucke et al. |

OTHER PUBLICATIONS

An International Search Report and a Written Opinion both dated Apr. 24, 2017, which issued during the prosecution of Applicant's PCT/IL2017/050028.

* cited by examiner

IMPEDANCE MONITORING DURING ELECTROSTIMULATION

FIELD OF THE INVENTION

The present invention relates to medical procedures, and specifically to electrostimulation of tissue.

BACKGROUND

Transcutaneous electrical nerve stimulation (TENS) is the use of electric current produced by a device to stimulate the nerves for therapeutic purposes. Electrical muscle stimulation (EMS), also known as neuromuscular electrical stimulation (NMES) or electromyostimulation, is the elicitation of muscle contraction using electric impulses.

U.S. Pat. No. 8,620,434, whose disclosure is incorporated herein by reference, describes a device and method for applying transcutaneous electrical nerve stimulation via an electrode. The device includes the electrode being arranged for detecting a change of a skin impedance and being configured for switching from a stimulation mode of operation for stimulating the nerve, into a recalibration mode of operation upon detection of the changed skin impedance. The device may include a plurality of electrodes being configured for detecting the change of the skin impedance and being configured for adjusting an electrical current flowing through the skin via the plurality of electrodes.

US Patent Application Publication 2004/0015212, whose disclosure is incorporated herein by reference, describes improved operating features for an electrotherapy device are provided by the use of a peel off detection system which monitors device operation and provides necessary corrective action where appropriate. More specifically, the electrotherapy device monitors the connection characteristics of the electrodes, in order to determine if acceptable connections are being maintained to the patient. In order to monitor these connections, a baseline signal measurement is made when the system is first started. Subsequent measurements are then compared to this baseline measurement, to insure that the magnitude stays within an acceptable range. If the measurement shows a non-acceptable connection condition, the electrotherapy device is shut down and appropriate warning signals are provided to the user. Where multiple output channels are used, isolation circuits are included in the feedback network in order to insure no signal coupling exists.

An article by Degen and Loeliger, entitled "An improved Method to continuously monitor the Electrode-Skin Impedance during Bioelectric Measurements," published in the Proceedings of the 29th Annual International Conference of the IEEE EMBS, 2007, which is incorporated herein by reference, describes a method that allows to monitor the electrode-skin impedance during bioelectric recordings in a continuous way, without reducing the common mode rejection ratio (CMRR) of the amplifier. The method is based on an additional common mode signal which is superimposed on the bioelectric signal.

U.S. Pat. No. 6,217,574, whose disclosure is incorporated herein by reference, describes an RF ablation system comprising an irrigated split tip electrode catheter, an RF generator and a signal processor. The catheter comprises four orthogonally arranged electrodes at the distal tip. The catheter is used to map the electrical activity of a heart chamber to locate site(s) of aberrant electrical pathways to be ablated. Once an ablation site has been located, the signal processor activates the RF generator to transmit a low level RF current to each electrode member of the split tip electrode. The signal processor receives signals indicative of the impedance between each electrode member and one or more surface indifferent electrodes and determines which electrode members are associated with the highest impedance. Such electrode members are those in greatest contact with the myocardium. The signal processor then automatically activates the RF generator to transmit an RF ablation current to the electrode members in contact with the myocardium to create a lesion.

SUMMARY OF THE INVENTION

There is provided, in accordance with some embodiments of the present invention, a method for controlling a stimulation procedure. The stimulation procedure is executed, by passing a plurality of stimulating pulses between a pair of electrodes coupled to skin of a subject. One or more reference pulses are passed between the pair of electrodes, the reference pulses being different from each of the stimulating pulses. An impedance between the electrodes is measured, using the reference pulses. In response to the impedance measured using the reference pulses, but not in response to any impedance measured using the stimulating pulses, the stimulation procedure is controlled.

In some embodiments, passing the reference pulses includes passing a plurality of reference pulses between respective pairs of the stimulating pulses.

In some embodiments, passing the plurality of references pulses includes passing the plurality of reference pulses at regular intervals.

In some embodiments, passing the reference pulses includes passing one or more symmetric reference pulses.

In some embodiments, passing the reference pulses includes passing one or more asymmetric reference pulses.

In some embodiments, measuring the impedance between the electrodes includes measuring the impedance by measuring a voltage between the pair of electrodes during the passing of the reference pulses.

In some embodiments, measuring the impedance between the electrodes includes measuring the impedance by measuring a current between the pair of electrodes during the passing of the reference pulses.

In some embodiments, passing the stimulating pulses between the pair of electrodes includes passing current-regulated stimulating pulses.

In some embodiments, passing the stimulating pulses between the pair of electrodes includes passing voltage-regulated stimulating pulses.

In some embodiments, passing the reference pulse before the stimulation procedure includes passing the reference pulse using a first supplied voltage that is lower than a second supplied voltage that is used to pass the stimulating pulses between the pair of electrodes.

In some embodiments, passing the reference pulses includes passing the reference pulses by substituting at least one pulse of the stimulation procedure with one of the reference pulses.

In some embodiments, passing the reference pulses includes passing the reference pulses without substituting any pulse of the stimulation procedure with one of the reference pulses.

In some embodiments, passing the reference pulses includes passing at least one reference pulse having a lower amplitude than an amplitude of at least one of the stimulating pulses.

In some embodiments, passing the at least one reference pulse includes passing at least one reference pulse having a current that is less than 15 mA.

In some embodiments, passing the at least one reference pulse includes passing at least one reference pulse having a current that is less than 10 mA.

In some embodiments, passing the at least one reference pulse includes passing at least one reference pulse having a current that is less than 5 mA.

In some embodiments, passing the at least one reference pulse includes passing at least one reference pulse having a voltage that is less than 15 V.

In some embodiments, passing the at least one reference pulse includes passing at least one reference pulse having a voltage that is less than 9 V.

In some embodiments, passing the reference pulses includes passing at least one reference pulse having a shorter duration than a duration of at least one of the stimulating pulses.

In some embodiments, passing the at least one reference pulse includes passing at least one reference pulse having a duration of less than 25 microseconds.

In some embodiments, passing the reference pulses includes passing at least one reference pulse having an amplitude that varies less than an amplitude of at least one of the stimulating pulses.

There is further provided, in accordance with some embodiments of the present invention, a controller for use with (i) stimulation circuitry that includes a pair of electrodes, and (ii) measuring circuitry. The controller includes at least one interface configured to couple the controller to the stimulation circuitry and measuring circuitry. The controller further includes controller circuitry, configured to, while the electrodes are coupled to skin of a subject, via the interface, (i) execute a stimulation procedure by driving the stimulation circuitry to pass a plurality of stimulating pulses between the pair of electrodes, (ii) drive the stimulation circuitry to pass one or more reference pulses between the pair of electrodes, the reference pulses being different from each of the stimulating pulses, and (iii) receive, from the measuring circuitry, an impedance between the electrodes that is measured using the reference pulses. The controller circuitry is further configured to, in response to the impedance measured using the reference pulses, but not in response to any impedance measured using the stimulating pulses, control the stimulation procedure.

In some embodiments, the controller circuitry is configured to control the stimulation procedure in response to the measured impedance by, via the interface, adjusting an amplitude of the stimulating pulses.

In some embodiments, the controller circuitry is configured to control the stimulation procedure in response to the measured impedance by generating an alert indicative of a required adjustment to the coupling of the electrodes to the skin.

In some embodiments, the controller circuitry is configured to drive the stimulation circuitry to pass the one or more reference pulses between the electrodes during the stimulation procedure.

In some embodiments, the controller circuitry is configured to control the stimulation procedure in response to the measured impedance by stopping the stimulation procedure.

In some embodiments, the controller circuitry is configured to:

receive, from the measuring circuitry, a baseline impedance between the electrodes and a subsequent impedance between the electrodes, and control the stimulation procedure in response to comparing the subsequent impedance to a threshold that is based on the baseline impedance.

In some embodiments, the controller circuitry is further configured to adaptively adjust the threshold during the stimulation procedure.

In some embodiments, the controller circuitry is configured to drive the stimulation circuitry to pass one of the reference pulses before the stimulation procedure, the baseline impedance being measured using the reference pulse that is passed before the stimulation procedure.

In some embodiments, the controller circuitry is configured to drive the stimulation circuitry to pass the reference pulse before the stimulation procedure using a first supplied voltage that is lower than a second supplied voltage that is used to pass the stimulating pulses between the pair of electrodes.

In some embodiments, the controller circuitry is configured to control the stimulation procedure in response to the measured impedance by, via the interface, controlling a supplied voltage that is used to pass the stimulating pulses between the pair of electrodes.

The present invention will be more fully understood from the following detailed description of embodiments thereof, taken together with the drawings, in which:

DETAILED DESCRIPTION OF EMBODIMENTS

Overview

In electrostimulation procedures, at least two electrodes are coupled (e.g., attached) to the skin of the subject, and subsequently, a plurality of stimulating pulses are passed between the electrodes. In current-regulated stimulation, a predefined amount of current is passed between the electrodes during each the stimulating pulses. In voltage-regulated stimulation, a predefined amount of voltage is applied between the electrodes during each of the stimulating pulses.

In some cases, the electrodes might not be properly coupled (e.g., attached) to the skin before the procedure. Alternatively or additionally, the electrodes may become at least partially uncoupled from the skin, or shorted to one another, during the procedure, e.g., due to movement of the subject or degradation of the adhesive material that keep the electrodes coupled to the skin. Such a scenario may lead to inefficient power consumption, and/or lessen the effectiveness of the stimulation. For example, if the impedance between the electrodes is higher than normal due to improper coupling of the electrodes to the skin, it may be necessary, for current-regulated stimulation, to increase the supplied voltage that supplies the stimulating current, thus consuming more power than would otherwise be necessary. For voltage-regulated stimulation, the increased impedance may cause a smaller amount of current to pass between the electrodes, thus lessening the effectiveness of the stimulation.

In light of the above, it may be advantageous, before and/or during the stimulation procedure, to measure the impedance between the electrodes, such that, if the measured impedance deviates from a particular threshold, the coupling (e.g., attachment) of the electrodes to the skin may be adjusted. To measure the impedance, the voltage between the electrodes may be measured while a current of known amplitude is passed between the electrodes. Alternatively, the current between the electrodes may be measured while a voltage of known amplitude is applied between the electrodes.

One implementation of the above-described impedance measurement is to measure the voltage or current between the electrodes while the stimulating pulses are passed between the electrodes. However, pulse parameters that are suitable for stimulation are not necessarily suitable for impedance measurement, and vice versa. For example, in many cases, the amplitude of the stimulating pulses varies over time in an "intra-pulse" and/or "inter-pulse" manner, thus rendering it difficult to use the stimulating pulses to accurately measure the impedance. That is, at least some of the stimulating pulses may have a varying amplitude, and/or the respective amplitudes of the stimulating pulses may be varied during the stimulation procedure, as the subject tries to find his "comfort zone."

In light of the above, embodiments of the present invention provide an improved implementation, in which one or more reference pulses are passed between the electrodes, in addition to the stimulating pulses. The reference pulses, but not the stimulating pulses, are used for impedance measurement, while the stimulating pulses, but typically not the reference pulses, are used for stimulation. Parameters such as pulse amplitude, duration, and frequency may be "tailored" differently for each type of pulse, thus facilitating effective stimulation and impedance monitoring. For example, in some embodiments of the present invention, the amplitude of the reference pulses is less time-varying than that of the stimulating pulses (and in fact, is often set to a constant value), thus allowing the reference pulses to be used to accurately measure the impedance between the electrodes.

System Description

Figure 1:
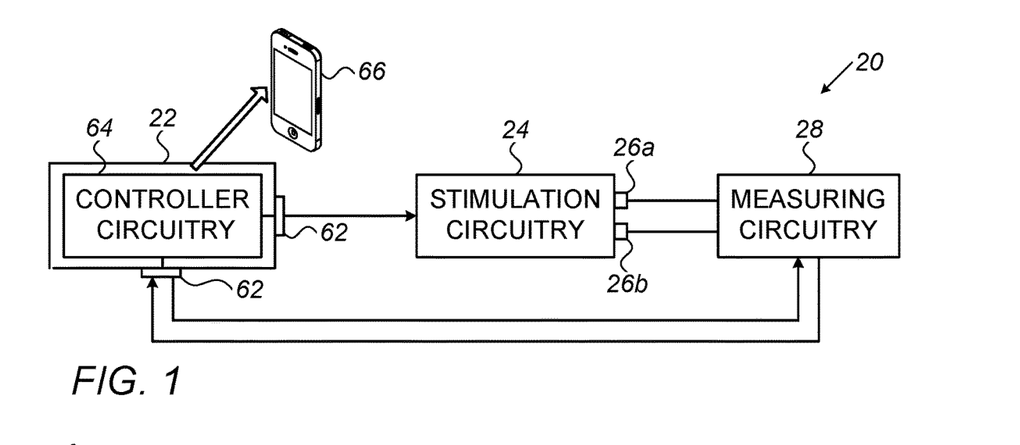
FIG. 1 is a block diagram of a system for applying, and monitoring impedance during, electrostimulation, in accordance with some embodiments of the present invention.

Reference is initially made to FIG. 1, which is a block diagram of a system 20 for applying, and monitoring impedance during, electrostimulation, in accordance with some embodiments of the present invention. System 20 comprises a controller 22 (e.g., a programmable controller configured to execute, for example, microcode), stimulation circuitry 24 comprising at least a pair of electrodes 26a and 26b, and measuring circuitry 28. Controller 22 comprises at least one interface 62 (e.g., an electric interface, such as a plug or socket) that couples the controller to stimulation circuitry 24 and measuring circuitry 28, and further comprises controller circuitry 64.

Electrodes 26a and 26b are coupled (e.g., attached) to skin of the subject who is to be electrostimulated. Subsequently, to execute the stimulation procedure, controller circuitry 64 drives stimulation circuitry 24 to pass a plurality of stimulating pulses between the electrodes. As further described hereinbelow, controller circuitry 64 may also drive the stimulation circuitry to pass one or more reference pulses between the pair of electrodes before and/or during the electrostimulation procedure, the reference pulses being different from each of the stimulating pulses. During the application of the reference pulses, but not during the application of the stimulating pulses, the controller circuitry drives measuring circuitry 28 to measure a voltage or current between the electrodes. The measuring circuitry passes the measured voltage or current to the controller circuitry, which then uses the quantity from the measuring circuitry to measure the impedance between the electrodes. In this manner, the reference pulses, but not the stimulating pulses, are used to measure the impedance. In any case, even if some impedances are measured using the stimulating pulses, the controller circuitry controls the stimulation procedure in response to impedance(s) measured using the reference pulses, but not in response to any impedance measured using the stimulating pulses.

Typically, at least one of the reference pulses is used to measure a baseline impedance between the electrodes. This reference pulse may be passed before the stimulation procedure (after coupling the electrodes to the skin), or during the procedure (e.g., near the beginning of the procedure). Subsequently, during the procedure, at least one reference pulse is used to measure a subsequent impedance between the electrodes, which, for ease of description, is referred to below as the "intraprocedural impedance." The intraprocedural impedance may be compared to a threshold that is based on the baseline impedance, and, in response thereto, the stimulation procedure may be controlled. For example, if the intraprocedural impedance deviates from the threshold, the controller circuitry may generate an alert that indicates that the coupling of the electrodes to the skin needs to be adjusted. (In some embodiments, the controller circuitry generates the alert by wirelessly or wiredly driving a smartphone 66 of the subject to display an appropriate message to the subject.) Further to receiving the alert, the subject may adjust the coupling (e.g., attachment) of the electrodes to the skin, e.g., by reapplying adhesive material at the electrode-skin interface for at least one of the electrodes.

In some embodiments, if the intraprocedural impedance deviates from the threshold, the controller circuitry stops the stimulation procedure, alternatively or additionally to generating the alert. While the stimulation procedure is stopped, the coupling (e.g., attachment) of the electrodes to the skin may be adjusted, and subsequently, the stimulation procedure may be restarted.

The above-described threshold may, for example, be a range of values having a lower bound that is slightly less than the baseline impedance, and an upper bound that is slightly greater than the baseline impedance, such that the intraprocedural impedance is considered to deviate from the threshold whether it is greater than the upper bound or lower than the lower bound. Alternatively, the threshold may be a single value (e.g., the baseline impedance plus or minus some margin), and the intraprocedural impedance may be considered to deviate from the threshold if it is greater than the threshold, or alternatively, if it is lower than the threshold.

In some embodiments, the threshold is adaptively adjusted during the stimulation procedure. For example, in some embodiments, the threshold is periodically lowered during the stimulation procedure, to account for the expected decrease in impedance during the procedure caused by sweating of the subject. Alternatively or additionally, the threshold may be adjusted in response to any other relevant factors.

Alternatively or additionally, in response to measuring the baseline and/or intraprocedural impedance between the electrodes, the amplitude of the stimulating pulses may be adjusted. For example, the amplitude of the stimulating current may be set as an increasing function of the measured impedance, since a higher impedance may be indicative of a greater amount of body fat in the subject, which, in turn, indicates that a stronger current is needed to reach the subject's nerve or muscle. Typically, the controller circuitry is configured to differentiate a stable, high-but-normal impedance from an abnormally high and/or increasing impedance. For the former type of impedance, the controller circuitry typically adjusts the amplitude of the stimulating pulses, as described immediately above. For the latter type of impedance, on the other hand, the controller circuitry typically generates an alert and/or stops the procedure, as described above.

Figure 2:
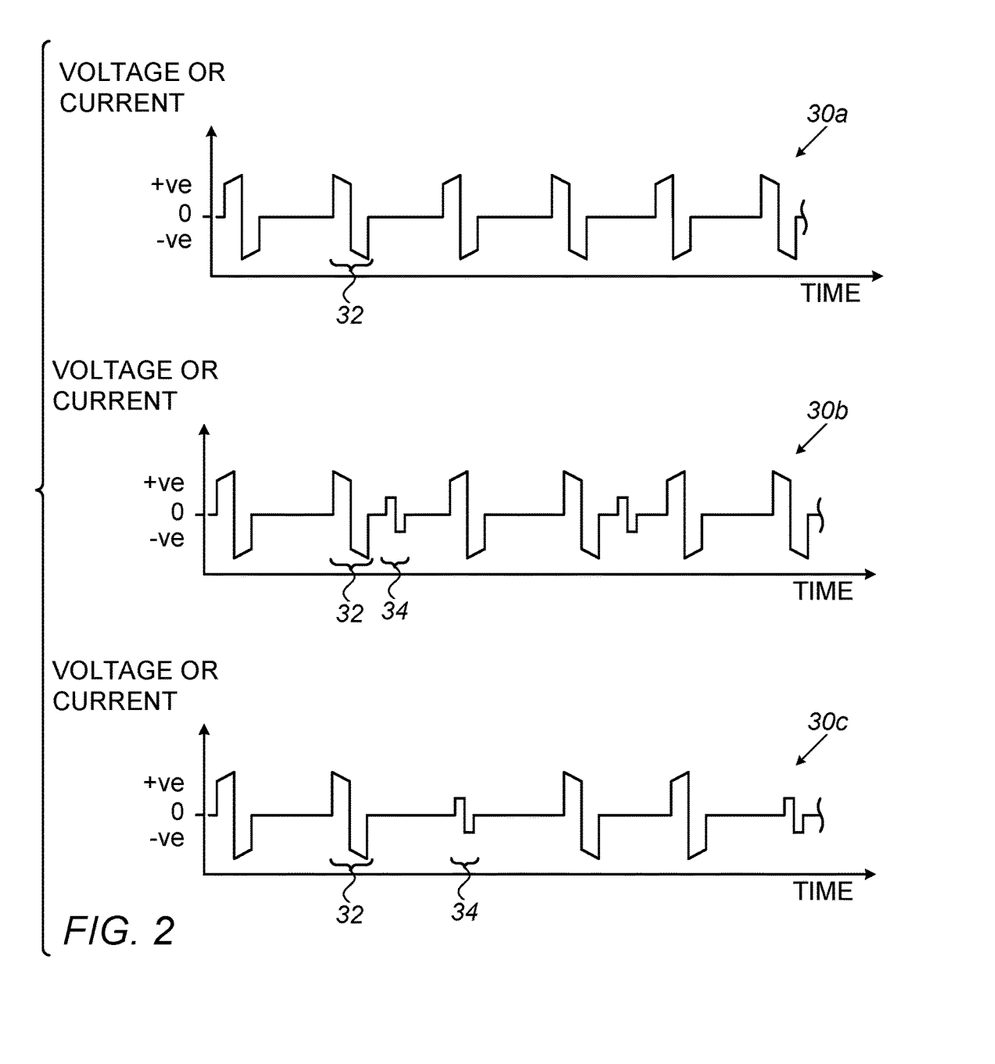
FIG. 2 is a schematic illustration of various pulse sequences that may be passed between electrodes, in accordance with some embodiments of the present invention.

Reference is now made to FIG. 2, which is a schematic illustration of various pulse sequences that may be passed between electrodes 26a and 26b, in accordance with some embodiments of the present invention. The pulses shown in FIG. 2 may be voltage pulses used for voltage-regulated stimulation, or alternatively, current pulses used for current-regulated stimulation. (Thus, the units of the vertical axes may be any appropriate unit for voltage or current.)

First sequence 30a is a sequence of stimulating pulses 32, which may be passed between the electrodes while executing a stimulation procedure. As shown in the figure, stimulating pulses 32 have varying intra-pulse amplitudes, such that it may be difficult to use the stimulating pulses to measure the impedance between the electrodes. (As noted above, the stimulating pulses may also vary in an inter-pulse manner, such that a particular pulse may have a different amplitude from that of a neighboring pulse.) Hence, in embodiments of the present invention, a sequence such as second sequence 30b or third sequence 30c, each of which includes a plurality of reference pulses 34 between respective pairs of stimulating pulses, is used, instead of first sequence 30a.

Reference pulses 34 typically have an amplitude that varies less than the amplitude of the stimulating pulses. For example, as shown in FIG. 2, each reference pulse may have a constant (i.e., "flat") positive ("+ve") amplitude, and a constant negative ("−ve") amplitude. Hence, as noted above, reference pulses 34, rather than stimulating pulses 32, may be more easily used to measure the impedance. Typically, as shown in FIG. 2, at least some of the reference pulses are passed at regular intervals (i.e., periodically), such that the impedance may be measured at regular intervals.

In some embodiments, at least one pulse of the stimulation procedure is substituted with one of the reference pulses. For example, in sequence 30c, two of the stimulating pulses of sequence 30a are substituted with respective reference pulses. In other embodiments, no pulse of the stimulation procedure is substituted with a reference pulse. For example, in sequence 30b, two reference pulses are added to sequence 30a, without replacing any of the stimulating pulses. Typically, the references pulses are added to the stimulating-pulse sequence (as in sequence 30b), rather than substituted for stimulating pulses (as in sequence 30c), unless the frequency of delivery of the stimulating pulses is too high to accommodate the addition of the reference pulses.

In some embodiments, as shown in FIG. 2, one or more of the reference pulses are symmetric. That is, for one or more of the reference pulses, the duration and amplitude of the positive portion of the pulse are equal to, respectively, the duration and amplitude of the negative portion of the pulse. Alternatively or additionally, one or more of the reference pulses may be asymmetric. (Even though the integral over an asymmetric pulse is typically zero, the amplitude and duration of the positive portion of the asymmetric pulse are different from the amplitude and duration of the negative portion of the pulse.)

Typically, as shown in FIG. 2, the reference pulses have an amplitude that is lower than that of the stimulating pulses, and/or a duration that is shorter than that of the stimulating pulses. Hence, the reference pulses are unlikely to stimulate the subject, and in fact, may not be noticed by the subject at all. For example, in some embodiments, the amplitude of the current of the reference pulses is less than 15 mA, such as less than 10 mA, e.g., less than 5 mA, and/or the voltage of the reference pulses is less than 15 V, e.g., less than 9 V. Alternatively or additionally, the duration of the reference pulses may be less than 25 microseconds.

Figure 3:
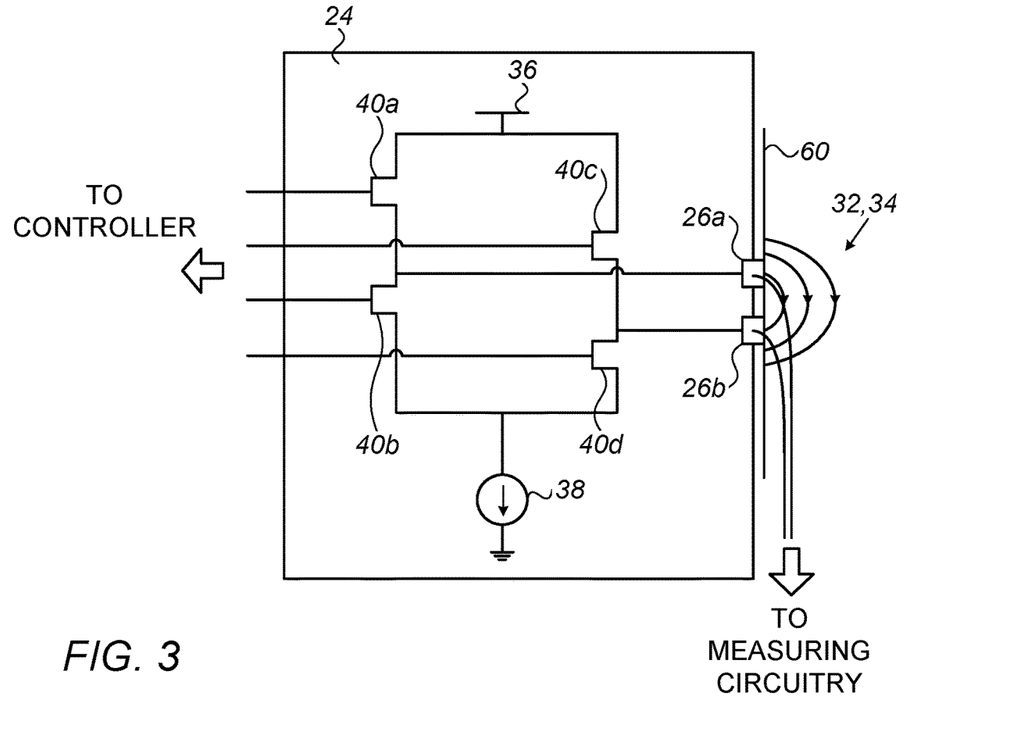
FIG. 3 is a schematic circuit diagram of stimulation circuitry coupled (e.g., attached) to skin of a subject, in accordance with some embodiments of the present invention.

Reference is now made to FIG. 3, which is a schematic illustration of stimulation circuitry 24 coupled (e.g., attached) to skin 60 of a subject, in accordance with some embodiments of the present invention. It is noted that the particular configuration shown in FIG. 3 is provided purely by way of example. In practice, any suitable circuitry may be used to apply the stimulating and reference pulses described herein, for either current-regulated or voltage-regulated applications.

In some current-regulated stimulation embodiments, stimulation circuitry 24 comprises the half-bridge circuit shown in FIG. 3. In such a circuit, a current source 38 supplies the current that is passed between electrodes 26a and 26b, while the voltage between the electrodes is limited to the voltage supplied by voltage supply 36. (In other words, the current that is passed between the electrodes is the minimum of "I" and "V/R," where "I" is the current supplied by current source 38, "V" is the voltage supplied by voltage supply 36, and "R" is the impedance of the tissue.) To generate pulses of current such as the stimulation and reference pulses shown in FIG. 2, the controller controls switches (e.g., transistor switches) 40a, 40b, 40c, and 40d. In particular, to pass current from electrode 26a to electrode 26b, the controller closes switches 40a and 40d, thus connecting electrode 26a to voltage supply 36 and electrode 26b to current source 38, while switches 40b and 40c remain open. Conversely, to pass current from electrode 26b to electrode 26a, the controller closes switches 40b and 40c, thus connecting electrode 26b to voltage supply 36 and electrode 26a to current source 38, while switches 40a and 40d remain open.

The direction of current determines the polarity of the pulse. For example, the respective positive portions of the pulses shown in FIG. 2 may be obtained by passing current from electrode 26a to electrode 26b, while the respective negative portions may be obtained by passing current from electrode 26b to electrode 26a. The degree to which the switches are closed determines the amplitudes of the pulses.

In some embodiments, the voltage supplied by voltage supply 36 is controlled, in response to the measured impedance. For example, in some embodiments, a "calibration procedure" is performed. At least one reference pulse, passed between the electrodes prior to the stimulation procedure, is used to measure the baseline impedance between the electrodes. Subsequently, the voltage supply 36 may be set to a voltage that is slightly higher than the product of the measured baseline impedance and the maximum desired stimulation current.

The above-described calibration procedure is advantageous, in that it facilitates setting a voltage limit that is high enough to accommodate the stimulation of the subject, yet not too high as to consume a relatively large amount of excess power. In other words, if the voltage supply were set without regard to the baseline impedance, the voltage supply would need to be set, for every subject, as high as needed to accommodate the "worst case scenario," i.e., the highest expected skin impedance. However, some subjects may have a skin impedance that is significantly lower than the highest expected skin impedance. For such subjects, the voltage supply would be too high, such that excess power would be needlessly consumed. Hence, by setting the voltage supply in response to the measured baseline impedance, an appropriate voltage limit may be set for each subject, thus facilitating more efficient consumption of power.

Typically, when passing the reference pulse that is used to measure the baseline impedance, the voltage supply is set to a lower voltage than the voltage to which it is subsequently set for the stimulation procedure. For example, the voltage supply may be set to a voltage that is slightly higher than the product of the maximum estimated impedance and the desired reference current. Subsequently, in response to the measured baseline impedance, the voltage supply may be increased in order to accommodate the stimulation, as described above. Since the precision of measuring circuitry 28 (FIG. 1) is typically greater for smaller supplied voltages than for larger supplied voltages, the above-described technique may facilitate a more precise measurement of the baseline impedance. (During the stimulation procedure, however, the voltage supply typically remains at the higher stimulation-accommodating value, even during the application of the reference pulses.)

For example, reference pulses such as those shown in FIG. 2 may have an amplitude of 10 mA, while skin impedance of human subjects is typically no higher than 1500 Ohm. Thus, during the calibration procedure, the voltage supply may be set to 18 V, which is slightly higher than the product of 10 mA and 1500 Ohm. Stimulation pulses such as those shown in FIG. 2 may have a maximum amplitude of 30 mA. Thus, if, for example, the measured baseline impedance was 1000 Ohm, the voltage supply for the stimulation procedure may be set to 35 V, which is slightly higher than the product of 30 mA and 1000 Ohm.

Figure 4:
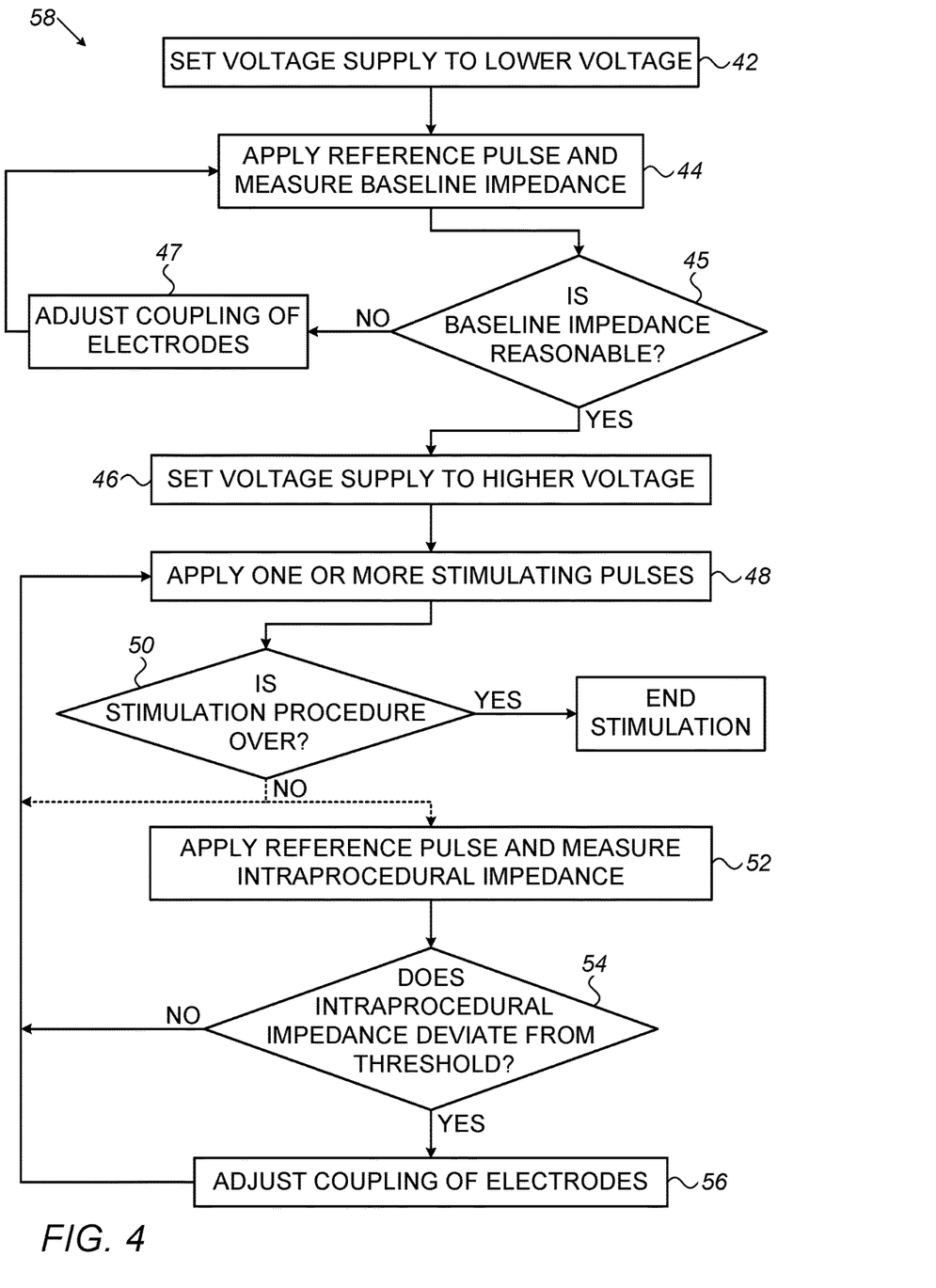
FIG. 4 is a flow diagram showing a method for electrostimulation practiced in accordance with some embodiments of the present invention.

Reference is now made to FIG. 4, which is a flow diagram showing a method 58 practiced in accordance with some embodiments of the present invention. Most of the steps in method 58 were already described above, but, for clarity, are again described hereinbelow, with reference to FIG. 4.

Method 58 begins with a first voltage-setting step 42, in which voltage supply 36 is set to a voltage that is high enough to accommodate a reference pulse, yet lower than the voltage used subsequently during the stimulation procedure. (As noted above, such a lower voltage may facilitate a more precise measurement of the baseline impedance.) Subsequently, in a baseline-impedance-measuring step 44, at least one reference pulse is applied to the subject by being passed between the electrodes, and during the application of the reference pulse, the baseline impedance is measured, by measuring the voltage between the electrodes. At a first decision step 45, the controller assesses whether the measured baseline impedance is reasonable, i.e., whether it falls within an expected range of normal human skin impedance, e.g., 300-1500 Ohm. If the baseline impedance is not reasonable (i.e., it is higher than expected, thus indicating that the electrodes may not have been properly coupled to the skin, or it is lower than expected, thus indicating a possible shorting of the electrodes), an alert may be generated, and subsequently, in response to the alert, the coupling (e.g., attachment) of the electrodes to the skin may be adjusted, at a first adjusting step 47. Subsequently, steps 44 and 45 are repeated. (Steps 42, 44, 45, and 47 collectively form part of the calibration procedure referred to above.)

Following an assessment that the baseline impedance is reasonable, at a second voltage-setting step 46, voltage supply 36 is set, in response to the baseline impedance, to a higher voltage that is high enough to accommodate the stimulation. Next, at a stimulating step 48, one or more stimulating pulses are applied to the subject, by being passed between the electrodes. At a second decision step 50, the controller, or the subject, decides whether the stimulation procedure is over, i.e., whether enough stimulating pulses have been applied to the subject. If the answer is affirmative, the stimulation procedure ends. Otherwise, depending on the current state of the stimulation procedure, either (i) more stimulating pulses are applied to the subject, at stimulating step 48, or (ii) at an intraprocedural-impedance-measuring step 52, at least one reference pulse is applied to the subject, and during the application of the reference pulse, the intraprocedural impedance between the electrodes is measured. Subsequently to (ii), at a third decision step 54, the controller compares the intraprocedural impedance to a threshold that is based on the baseline impedance. If the intraprocedural impedance deviates from the threshold (i.e., it is higher than the threshold, thus indicating a possible decoupling of the electrodes from the skin, or it is lower than the threshold, thus indicating a possible shorting of the electrodes), an alert may be generated, and subsequently, in response to the alert, the coupling (e.g., attachment) of the electrodes to the skin may be adjusted, at a second adjusting step 56. Following the adjustment, the stimulation may continue, at stimulating step 48.

In some embodiments, controller circuitry 64 is embodied as a programmable digital computing device comprising a central processing unit (CPU) and random access memory (RAM). Program code, including software programs, and/or data are loaded into the RAM for execution and processing by the CPU. The program code and/or data may be downloaded to the controller in electronic form, over a network, for example, or it may, alternatively or additionally, be provided and/or stored on non-transitory tangible media, such as magnetic, optical, or electronic memory. Such program code and/or data, when provided to the controller, produce a machine or special-purpose computer, configured to perform the tasks described herein.

It will be appreciated by persons skilled in the art that the present invention is not limited to what has been particularly shown and described hereinabove. Rather, the scope of the present invention includes both combinations and subcombinations of the various features described hereinabove, as well as variations and modifications thereof that are not in the prior art, which would occur to persons skilled in the art upon reading the foregoing description.

The invention claimed is:
1. A method for use with tissue of a subject, comprising:
performing a calibrating procedure by:
passing a calibration-reference pulse via a pair of electrodes, while the pair of electrodes are coupled to the subject's tissue;

measuring impedance between the electrodes using the calibration-reference pulse, and designating the measured impedance as a baseline impedance for the subject; and setting a voltage supply to a current source for the electrodes to be higher than a product of the baseline impedance for the subject and a maximum desired stimulation current;

subsequently:

using the current source, performing a stimulation procedure, by passing a plurality of stimulating pulses between the pair of electrodes, while the pair of electrodes are coupled to the subject's tissue;

passing one or more intraprocedural-reference pulses between the pair of electrodes, the reference pulses being different from each of the stimulating pulses;

measuring an intraprocedural impedance between the electrodes, using the intraprocedural-reference pulses;

comparing the intraprocedural impedance to a threshold that is based upon the baseline impedance for the subject; and in response to the comparing, controlling the stimulation procedure.

2. The method according to claim 1, wherein controlling the stimulation procedure comprises adjusting an amplitude of the stimulating pulses.

3. The method according to claim 1, wherein controlling the stimulation procedure comprises generating an alert indicative of a required adjustment to the coupling of the electrodes to the subject's tissue.

4. The method according to claim 1, wherein controlling the stimulation procedure comprises stopping the stimulation procedure.

5. The method according to claim 1, wherein passing the intraprocedural-reference pulses comprises passing a plurality of intraprocedural-reference pulses between respective pairs of the stimulating pulses.

6. The method according to claim 5, wherein passing the plurality of intraprocedural-references pulses comprises passing the plurality of intraprocedural-reference pulses at regular intervals.

7. The method according to claim 1, wherein passing the intraprocedural-reference pulses comprises passing one or more symmetric intraprocedural-reference pulses.

8. The method according to claim 1, wherein passing the intraprocedural-reference pulses comprises passing one or more asymmetric intraprocedural-reference pulses.

9. The method according to claim 1, wherein measuring the intraprocedural impedance between the electrodes comprises measuring the intraprocedural impedance by measuring a voltage between the pair of electrodes during the passing of the intraprocedural-reference pulses.

10. The method according to claim 1, wherein measuring the intraprocedural impedance between the electrodes comprises measuring the intraprocedural impedance by measuring a current between the pair of electrodes during the passing of the intraprocedural-reference pulses.

11. The method according to claim 1, wherein passing the stimulating pulses between the pair of electrodes comprises passing current-regulated stimulating pulses.

12. The method according to claim 1, wherein passing the stimulating pulses between the pair of electrodes comprises passing voltage-regulated stimulating pulses.

13. The method according to claim 1, further comprising adaptively adjusting the threshold during the stimulation procedure.

14. The method according to claim 1, wherein passing the calibration-reference pulse before performing the stimulation procedure comprises passing the calibration-reference pulse using a first supplied voltage that is lower than the voltage supply that supplies the current source that is used to pass the stimulating pulses between the pair of electrodes.

15. The method according to claim 1, wherein passing the intraprocedural-reference pulses comprises passing the intraprocedural-reference pulses by substituting at least one pulse of the stimulation procedure with one of the intraprocedural-reference pulses.

16. The method according to claim 1, wherein passing the intraprocedural-reference pulses comprises passing the intraprocedural-reference pulses without substituting any pulse of the stimulation procedure with one of the intraprocedural-reference pulses.

17. The method according to claim 1, wherein passing the intraprocedural-reference pulses comprises passing at least one intraprocedural-reference pulse having a lower amplitude than an amplitude of at least one of the stimulating pulses.

18. The method according to claim 17, wherein passing the at least one intraprocedural-reference pulse comprises passing at least one intraprocedural-reference pulse having a current that is less than 15 mA.

19. The method according to claim 18, wherein passing the at least one intraprocedural-reference pulse comprises passing at least one intraprocedural-reference pulse having a current that is less than 10 mA.

20. The method according to claim 19, wherein passing the at least one intraprocedural-reference pulse comprises passing at least one intraprocedural-reference pulse having a current that is less than 5 mA.

21. The method according to claim 17, wherein passing the at least one intraprocedural-reference pulse comprises passing at least one intraprocedural-reference pulse having a voltage that is less than 15 V.

22. The method according to claim 21, wherein passing the at least one intraprocedural-reference pulse comprises passing at least one intraprocedural-reference pulse having a voltage that is less than 9 V.

23. The method according to claim 1, wherein passing the intraprocedural-reference pulses comprises passing at least one intraprocedural-reference pulse having a shorter duration than a duration of at least one of the stimulating pulses.

24. The method according to claim 23, wherein passing the at least one intraprocedural-reference pulse comprises passing at least one intraprocedural-reference pulse having a duration of less than 25 microseconds.

25. The method according to claim 1, wherein passing the intraprocedural-reference pulses comprises passing at least one intraprocedural-reference pulse having an amplitude that varies less than an amplitude of at least one of the stimulating pulses.

26. A controller for use with (i) stimulation circuitry that includes a pair of electrodes, a current source for the electrodes, and a voltage supply to the current source, (ii) measuring circuitry, and (iii) tissue of a subject, the controller comprising:

at least one interface configured to couple the controller to the stimulation circuitry and measuring circuitry; and controller circuitry, configured, via the interface:

to perform a calibrating procedure by:

driving the stimulation circuitry to pass a calibration-reference pulse via the pair of electrodes, while the pair of electrodes are coupled to the subject's tissue;

receiving from the measuring circuitry an impedance between the electrodes that is measured using the calibration-reference pulse, and designating the measured impedance as a baseline impedance for the subject; and setting the voltage supply to be higher than a product of the baseline impedance for the subject and a maximum desired stimulation current; and subsequently:

using the current source to perform a stimulation procedure by driving the stimulation circuitry to pass a plurality of stimulating pulses between the pair of electrodes, while the pair of electrodes are coupled to the subject's tissue, to drive the stimulation circuitry to pass one or more intraprocedural-reference pulses between the pair of electrodes, the reference pulses being different from each of the stimulating pulses, and to receive, from the measuring circuitry, an intraprocedural impedance between the electrodes that is measured using the intraprocedural-reference pulses, to compare the intraprocedural impedance to a threshold that is based upon the baseline impedance for the subject; and in response to the comparing, to control the stimulation procedure.

* * * * *